United States Patent [19]

Kornberg

[11] Patent Number: 4,562,596
[45] Date of Patent: Jan. 7, 1986

[54] AORTIC GRAFT, DEVICE AND METHOD FOR PERFORMING AN INTRALUMINAL ABDOMINAL AORTIC ANEURYSM REPAIR

[76] Inventor: Elliot Kornberg, Suite 416, Cape Royal Bldg., 1980 N. Atlantic Ave., Cocoa Beach, Fla. 32931

[21] Appl. No.: 603,800

[22] Filed: Apr. 25, 1984

[51] Int. Cl.⁴ .......................... A61F 1/24; A61F 1/22; A61B 17/00
[52] U.S. Cl. .................................. 623/1; 128/334 R; 128/325
[58] Field of Search .................... 3/1.4, 1; 128/334 R, 128/334 C, 343, 1 R, 325

[56] References Cited
U.S. PATENT DOCUMENTS

| 2,845,959 | 3/1956 | Sidebotham | 139/387 |
| 2,978,787 | 4/1961 | Liebig | 28/73 |
| 3,874,388 | 4/1975 | King et al. | 128/334 R |
| 3,882,845 | 5/1975 | Bucalo | 128/334 R X |
| 3,908,662 | 9/1975 | Razgulov et al. | 128/334 R |
| 4,007,743 | 2/1977 | Blake | 128/334 R |
| 4,140,126 | 2/1979 | Choudhury | 128/325 |
| 4,167,045 | 9/1979 | Sawyer | 3/1.4 |
| 4,190,909 | 3/1980 | Ablaza | 3/1.4 |
| 4,202,349 | 5/1980 | Jones | 128/689 |
| 4,204,526 | 5/1980 | Samuels et al. | 128/1 R |
| 4,229,838 | 10/1980 | Mano | 3/1.4 |
| 4,286,341 | 9/1981 | Greer et al. | 3/1.4 |
| 4,309,776 | 1/1982 | Berguer | 3/1 |
| 4,313,231 | 2/1982 | Koyamada | 3/1.4 |
| 4,355,426 | 10/1982 | MacGregor | 3/1.4 |
| 4,425,908 | 1/1984 | Simon | 128/1 R |

Primary Examiner—Richard J. Apley
Assistant Examiner—Alan W. Cannon
Attorney, Agent, or Firm—Beveridge, DeGrandi & Weilacher

[57] ABSTRACT

An aortic graft that is specifically constructed for intraluminal insertion and comprising a flexible hollow, tubular material, having a generally cylindrical shape with an upper end and lower end and having a minor and major axis, and having disposed along its major axis a plurality of parallel struts, the struts having angled hooks with barbs at their upper ends, the upper ends of the struts extending beyond the upper end of the tubular material, thus allowing the graft to be securely attached to the inside of the aorta above the aneurysm. A tubular device for inserting the graft is also disclosed.

9 Claims, 10 Drawing Figures

U.S. Patent Jan. 7, 1986 Sheet 1 of 2 4,562,596
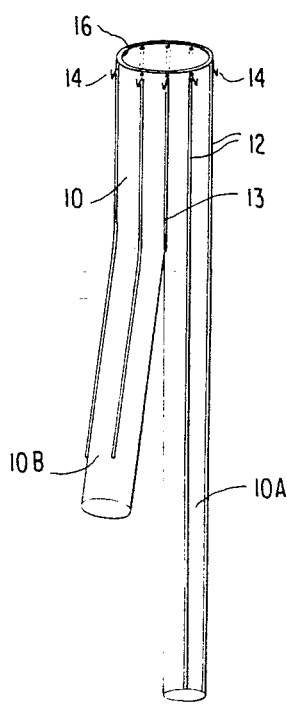
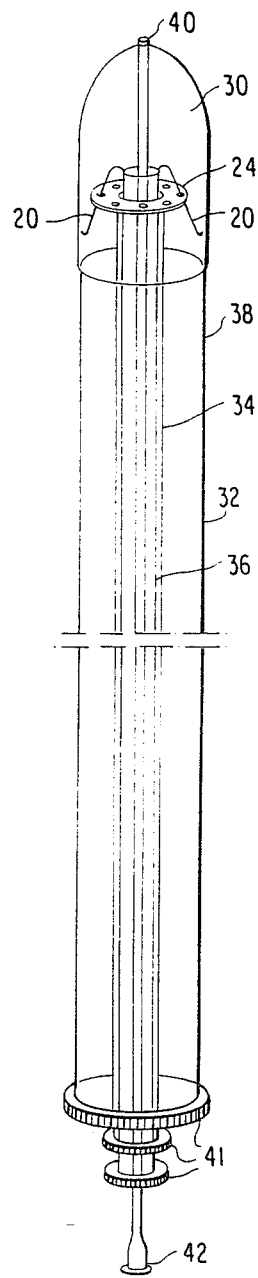
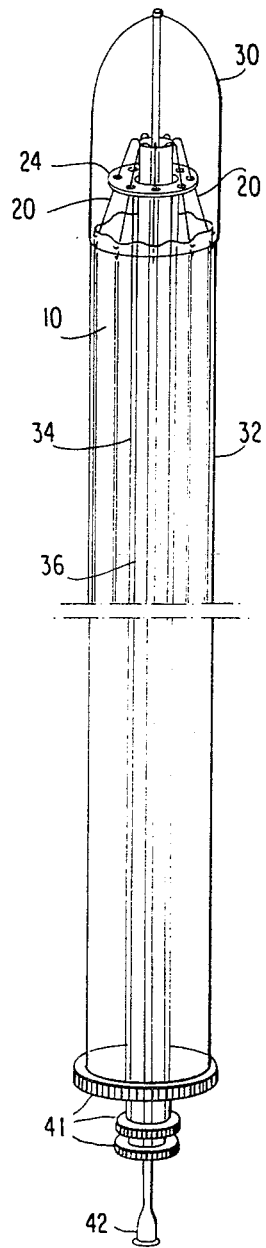
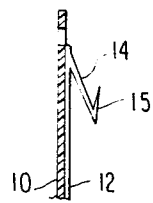
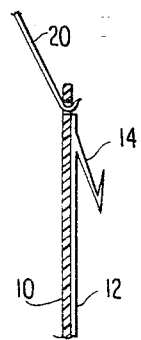

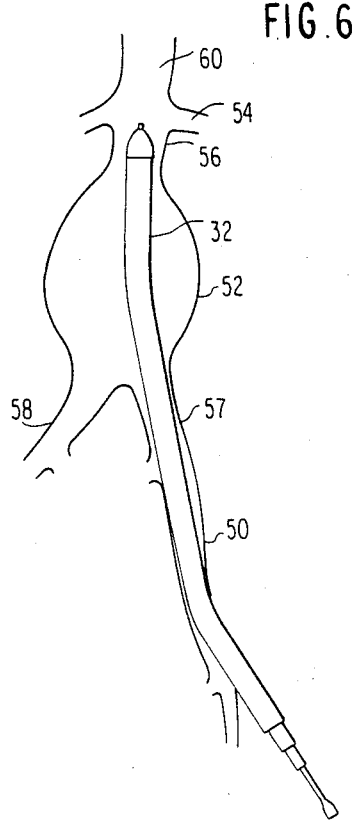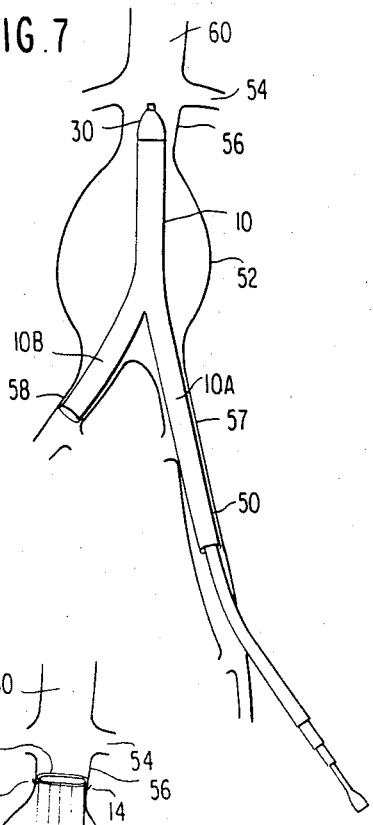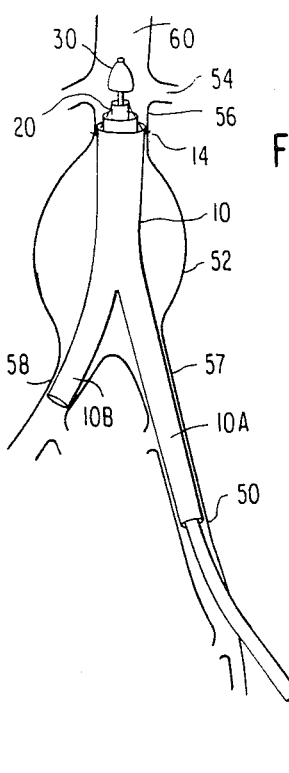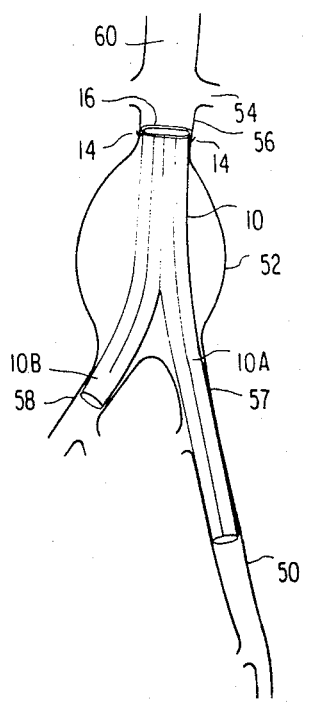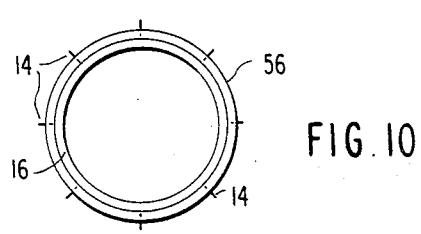

AORTIC GRAFT, DEVICE AND METHOD FOR PERFORMING AN INTRALUMINAL ABDOMINAL AORTIC ANEURYSM REPAIR

The invention concerns an aortic graft, a device and method for the intraluminal repair and treatment of abdominal aortic aneurysms.

An abdominal aortic aneurysm is a sac caused by an abnormal dilation of the wall of the major artery of the body as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk from which the systemic arterial system proceeds. It arises from the left ventricle of the heart, passes upward, bends over and passes down through the thorax and through the abdomen to about the level of the fourth lumbar vertebra, where it divides into the two common illiac arteries.

The aneurysm usually arises in the infrarenal portion of the arterioscleroticly diseased aorta, i.e. below the kidneys. When left untreated, the aneursym will eventually cause rupture of the sac with ensuing fatal hemorrhaging in a very short time. The high mortality associated with the rupture has lead to the present state of the art and the transabdominal surgical repair of abdominal aortic aneursyms. Surgery involving the abdominal wall, however, is a major undertaking with associated high risk. There is considerable mortality and morbidity associated with this magnitude of surgical intervention which in essence involves replacing the diseased and aneurysmal segment of blood vessel with a prosthetic device which is a synthetic tube, usually fabricated of either Dacron (a polyester), polytetrafluoroethylene, or other suitable material.

If the aneurysmal segment of the aorta can be functionally excluded from the pressures of the blood flow then the condition can be treated even without excising the diseased segment of aorta.

It is therefore the object of this invention to provide a method to exclude the aneurysmal segment of abdominal aorta from the circulation without the need for major abdominal surgery.

A further object of this invention is to reduce the mortality and morbidity associated with an extensive abdominal operation and the need for a general anesthetic in patients who usually have other associated diseases.

A still further object of this invention is to allow for the emergency stabilization of patients with ruptured abdominal aortic aneurysms.

A still further object of the invention is to provide a method for treatment of abdominal aortic aneurysms without the need for surgical intervention through the abdominal wall.

A further object of the invention is to provide a device for repair of abdominal aortic aneurysms which will reduce the mortality and morbidity associated with major abdominal surgery.

In achieving these and other objects, one feature of the invention resides in a method whereby a vascular graft of a new configuration is inserted into the inside of the aorta through a cutdown in the femoral artery. In this way, the aneurysmal segment of the abdominal aorta is excluded from the circulation system. A cutdown is a creation of a small, incised opening, especially over a vein or other critical vessel.

A further feature of the invention resides in a method employing a tubular device having mounted therein a new vascular graft and comprising forming an opening in a femoral artery, inserting a vascular graft into the artery and moving the graft in an upwardly direction into the aorta without the need for general anesthetic.

A still further feature of the invention resides in a device made of a plurality of tubes having a generally cylindrical configuration and having mounted therein the new vascular graft structure, which device is designed for easy operation in positioning the graft in the desired location in the damaged artery.

Additionally, a feature of the invention resides in a tubular graft material having a plurality of struts or stays equipped with hooks for rapid and secure attachment within the desired location of the damaged artery.

The nature and characteristic features of the present invention will be better understood through the following detailed description and accompanying drawings wherein:

FIG. 1 shows an aortic bifurcation graft used in accordance with the invention. The graft is equipped with a circumferential row of hooks and a plurality of longitudinal struts.

FIG. 2 shows an enlarged view of the upper end of a strut and hook.

FIG. 3 shows the tubular device of the invention used to insert a graft.

FIG. 4 shows the tubular device of the invention containing the graft encased within it and ready for intraluminal insertion.

FIG. 5 shows a portion of the means for holding the graft inside the tubular device.

FIG. 6 shows the device with the encased graft being inserted inside the aorta through a femoral artery cutdown.

FIG. 7 shows the strut supported graft being positioned into the other illiac artery and above the aneurysm.

FIG. 8 shows the deployment and attachment of the graft proximally to the aorta above the aneurysm.

FIG. 9 shows the graft in place and excluding the aneurysm from the circulation.

FIG. 10 is a cross sectional view through the proximal end of the graft and aorta showing the circumferential attachment of the graft to the aorta.

The invention will now be described in further detail with reference to the drawings.

In FIG. 1, the bifurcated graft 10 with its supporting struts 12 is illustrated. Since the purpose of this invention is to permanently place the vascular graft intraluminally to exclude the aneurysm from the blood flow, then the graft must have support along its length, so that the blood flow does not dislodge it, over the lifetime of the patient. The flexible conduit 10 which constitutes the bifurcated graft of this invention is sufficiently flexible to be capable of conforming to the interior contour of the wall portion of the artery into which it is inserted. The graft is a generally cylindrical, hollow, bifurcated sleeve with longitudinal supporting and reinforcing members called struts 12 running along the major axis of the cylindrical sleeve. The struts assure proper orientation of the graft within the artery. The bifurcated graft 10 has two legs, with one leg thereof 10A generally being longer than the other 10B.

A variety of different configurations may be used so that the number of circumferential located strengthening struts or ribs 12 attached or formed in the wall of the graft may vary from a minimum of four up to twelve or more, preferably eight. The upper limit on the number of struts is not critical provided that no more are used than is necessary. Of course with more struts, the graft becomes increasingly more rigid.

The struts or strays may be formed of any suitable material, surgical steel being an example of one such substance. Being preferably formed of steel, the struts permit the graft to be readily observed by X-ray visualization techniques during deployment in the artery. The degree of flexibility of the struts can vary provided that the vascular graft is sufficiently rigid to perform in accordance with the method of the invention.

The struts can run the length of each leg or only part of the entire length of each leg of the graft. Typically, the struts will run essentially the entire length of each leg or a majority of the distance along each leg. Generally, each graft will have three different size of struts; namely, a long strut for the long leg 10A, a shorter strut for the shorter leg 10B, and an even shorter strut 13 which will extend from the circular opening 16 at the top of the graft to the point of bifurcation.

The material of the graft may typically be fabricated from flexible natural or synthetic polymeric substances such as polyester fabric (DACRON), polytetrafluoroethylene and the like. Other substances such as Mylar, rayon, cellulose acetate, cellulose butyate may also be used. These substances may be specially woven and/or treated textile fabric material inert to body fluids and compatible therewith. Many such biologically compatible materials are known in the art and may be used for purposes of this invention. Typically, these materials are very thin, on the order of 0.5 mm.

Generally, the graft is prepared and packaged under aseptic conditions to avoid contamination. It is further contemplated that the graft may be treated with non-wettable substance such as liquid silicone or wax. It may also be cleaned with an antibiotic prior to use. Further, it may be treated with an anticoagulant. All such techniques are known in the art and may be used according to the present invention as desired or necessary.

The length of each leg of the graft can be determined by experience and will vary somewhat depending on the patient. The graft is characterized by 3 important dimensions; namely, the length of the single tube of the graft before the point or bifurcation, the length of the short leg 10B and the length of the long leg 10A. Generally, the upper tubular section will range from 5 to 10 cm, the short leg 10 will range from 5 to 15 cm and the longer leg will range from 15 to 20 cm. The lengths of the long and short leg can be tailored in the operating room to fit the intended patient. It is for this reason that the struts may not go to the complete end of each leg; that is, in order to enable the surgeon to cut off a short piece of the end of the leg to tailor it to the specific patient.

The proximal attachment of the graft 10 to the inside wall of the aorta is accomplished by the hooks 14 which are located at the upper end of each strut 12. The row of hooks 14 forms a ring around the outer circumference of graft 10 and are oriented downwardly at an angle of about 10°–45° C. with respect to the vertical. Each hook 14 has a barb 15 located at the lower end of the hook so as to inhibit upward movement which might tend to dislodge the graft after it is positioned and attached to the aorta wall. While FIG. 1 shows a hook 14 at the upper end of each strut 12, it is to be understood that the hooks could be fewer in number than the number of struts; e.g. the hooks could be attached to every other strut.

A flexible ring 16 located at the upper end of the graft 10 functions to exclude the multiple punctures in the aorta, where the hooks 14 pierce the blood vessel, from the blood flow after the graft is set in position. The ring 16 may be fabricated of flexible, resilient plastic or rubber which is in the compressed, or partially open state prior to positioning in the damaged artery. Once in place, the ring will spring open and snug up against the walls of the artery covering the punctures in the arterial wall made by the hooks 14. It is contemplated that a graft could also be made without the resilient ring 16.

The graft has struts 12 that run for essentially the length of the strut along its longest leg 10A as well as midline struts 13 which extend only to the bifurcation of the graft 10. This gives added longitudinal support to the graft when it is in place. It also gives more flexibility to the other or shorter graft limb 10B, so that it can be positioned more easily into the other side. The struts may be formed of any biologically acceptable material such as surgical steel or even plastic of sufficient rigidity and preferably radiologically opaque to permit visualization during the positioning of the graft in the patient.

In FIG. 2, the upper end of the strut 12 is shown with the hook 14 coming off at about a 30 degree angle. At the uppermost end of strut 12, there is formed an eyelet or opening to permit temporary engagement with other holding means to be described below. Preferably, the barb 15 on the lower end of hook 14 is oriented parallel to the strut 12. This allows a firm anchoring into the tissues and also lessens the risk of damaging surrounding organs. Although the preferred embodiment of the invention includes the formation of the hook 14 as shown in FIG. 2, it is contemplated that other fastening means may be suitably used for this purpose such as clips, needles or any permanent suture material. The barb 15 at the end of the hook 14 is only a fraction of the length of the hook, typically 2 to 8 mm. Because the barb 15 is preferably parallel to the strut, it lies in a safe manner parallel to any other organs so as to prevent damage thereto and to further limit cutting back through aorta. The hook 14 and barb 15 may be formed of the same material as the strut 12.

In FIG. 3, the tubular positioning device 32 of the invention is shown without the graft in place. The device comprises a plurality of concentrically arranged sliding tubes including an outer casing or tube 38 fitted with a separable bullet shaped upper top 30 and which together form a cylindrical hollow outer housing. Outer casing 38 is removed by slipping or pulling it off prior to deployment. Contained within the outer hollow tubular housing 38 is hollow, generally cylindrical tube 36, the major axis of which coincides with the major axis of the housing 38. At the upper end of tube 36 are fastened a plurality of arms 20. Only two of such arms 20 are shown in FIG. 3 but it is to be understood that the number of arms 20 coincide with the number of hooks 14 eyelets. The arms 20 are shaped so as to readily engage with the eyelet formed at the top end of strut 12.

A second hollow, generally cylindrical tube 34 is in sliding engagement over the first, or inner, tube 36. A fenestrated collar or ring 24 is attached at the upper end of the outer tube 34. Tube 34 in the position shown in FIG. 3 is located somewhat below the top of inner tube 36. Arms 20 are attached at the upper edge of tube 36 and pass downwardly through the fenestrations in ring 24. The arms flair gently outwardly towards the interior perimeter wall of top 30 and when at rest hang essentially vertically downward. Thus, by moving inner tube 34 with respect to tube 36 in an upwardly or downwardly direction, the arms 20 attached at the top of tube 34 are movable therein as limited by the size of the fenestrations and can be opened and closed similar to the ribs on an umbrella. All tubular members may be formed of flexible plastic or metal. It is important that the material be radioopaque so that the location of the apparatus can be easily seen on visualizing equipment employed during deployment of the graft in the patient.

The outer casing 38 fits snugly into the under surface of a bullet shaped capsule 30 and acts as a protective sleeve for the graft prior to use. Prior to depoyment of the graft, the casing 38 may be slipped off and disposed of. This allows easy passage of the device through the artery. The capsule 30 is secured by a centrally located hollow tube 40 inside tube 36 which passes up through the casing 38 from its lower end, through which angiography can also be performed. At the lower end of the device there are three lock nuts 41 or other suitable fastening means. These serve the dual purpose of securing the sliding tubes 36 and 34 in place and providing a blood tight seal as the procedure is performed. A connector 42 for angiography is also provided but is an optional feature of the device. A syringe (not shown) may be attached to 42 for this purpose. The fastening means 41 can be the same or different and are in staggered arrangement as shown in order to prevent impingement on each other. All the tubes 40, 36 and 34 are nested together as shown in the drawings and are movable relative to each other by pulling or pushing motion. The diameter and overall dimensions of device 32 is not narrowly critical and may vary depending on the patient. The upper limit in size is clearly that which will just fit into the artery and the lower limit will be that dimension which will enable all components and the graft to be contained therein.

In FIG. 4, the device 32 is shown with the graft 10 loaded inside and ready for insertion into the aorta. The graft is inserted from below at the lower end of casing 38 and is gently pushed up until the lower end of arms 20 which have a hook or other single fastening means formed therein engage with the upper end of the strut 12. The upper end of strut 12 can have an eyelet, hook, loop, ring or any other suitable fastening means formed integral therewith for rapid and simple disengagable connection with arms 20. The graft 10 would be loaded at the place of manufacture and the entire device suitably packaged as, for example, in a "blister" pack and would be marketed as a disposable item. The protective casing 38 keeps the preloaded graft 10 neatly folded up inside and when ready for use is inserted into the cutdown and then slipped out when ready for deployment.

FIG. 5 shows in detail how the device arm hook 20 engages with the eyelet hole in the upper end of the strut 12.

In FIG. 6, the graft loaded device 32 shown in the process of insertion through a cutdown inside the aorta 60. The usual location of the anuerysm 52 in relationship to the renal arteries 54 and the neck of the aneurysm 56 is shown. The right 58 and left 57 illiac arteries and the femoral 50 artery are also shown. At this stage, the short leg 10B is still folded against the longer of the two legs 10A. At the appropriate point when blood flow begins to enter the graft, the shorter leg 10B floats free in the blood stream and may be directed to the proper position.

In FIG. 7, the graft 10 is shown being positioned at the neck of the aneurysm 56 below the renal arteries 54 after the free graft limb 10B has been floated into position in the right illiac artery 58.

In FIG. 8, the capsule 30 has been elevated off of the upper end of the graft 10 by pushing on small inner tube 40. The arms 20 of the device have been opened by pushing upwardly on tube 34 and the hooks 14 have been set into the aortic wall by gentle downward traction on the device. The device arms are then collapsed by pulling downwardly on tube 40 so as to lower capsule 30 onto the arms 20 and the device is removed through the inside of the graft by pulling it out. The size of the capsule 30 and the graft limb are such that the graft limb is snugged into place in the illiac artery as the device is withdrawn out of that artery.

In FIG. 9, the graft 10 is shown in place. The aneurysm 52 is excluded from the circulation. The small cutdown opening in the femoral artery 50 has been repaired by standard vascular surgical technique. The downward flow of blood holds the distal graft limbs 10A and 10B in place so that no mechanical attachment is necessary distally. There is no danger of collapse of the distal end of the tubes 10A and 10B even if struts 12 do not go to the entire length of the limbs. The flow mechanism of the blood keeps the graft open. Ring 16 is shown in its sprung open position fitting snugly against the arterial wall just above the location of the aneurysm. The material of the ring 16 can be any biologically acceptable substance such as a resilient silicone rubber. Functioning to keep the graft fully expanded, ring 16 fits up against the arterial wall 56 so the blood does not run between the graft and the arterial wall. Leakage of blood into the area of the aneurysm is thereby minimized.

The proximal attachment of the graft is shown in cross section in FIG. 10. The aortic wall at the neck of the aneurysm 56 is pierced by the multiple radially placed hooks 14. These puncture wounds are then excluded from the blood flow by the snug fit provided by the flexible ring 16 at the top of the graft. This then accomplishes the goal of excluding the abdominal aortic aneurysm from the circulation.

Depending on the site of rupture, this method and device would be used instead of or in preparation for the standard abdominal approach. This would greatly reduce the considerable mortality and morbidity associated presently with abdominal aortic aneurysmectomy for ruptured aneurysms.

It should be noted that there can be variations of this device and grafting procedure, such as using a straight tube graft rather than the bifurcation graft, that is illustrated, which do not depart from the spirit and scope of the present invention and are intended to be encompassed by the claims appended hereto.

I claim:

1. An aortic graft that is specifically constructed for intraluminal insertion and comprising a flexible hollow, tubular material, having a generally cylindrical shape with an upper end and lower end and having a minor and major axis, and having disposed along its major axis a plurality of parallel struts, the struts having angled hooks with barbs at their upper ends, the upper ends of the struts extending beyond the upper end of the tubular material, thus allowing the graft to be securely attached to the inside of the aorta above the aneurysm.

2. The aortic graft of claim 1, wherein the material is a material or synthetic fabric material inert to body fluids.

3. The aortic graft of claim 1, further comprising at least 4 struts arranged essentially parallel to the major axis thereof.

4. The aortic graft of claim 1 further comprising the upper end of said struts having fastening means above said angled hooks.

5. The aortic graft of claim 4, further comprising fastening means which are eyelets.

6. The aortic graft of claim 1, further comprising wherein the angled hooks are in a downward and outward direction from 10° to 45°.

7. The aortic graft of claim 6, further comprising wherein the barbs on said angled hooks are parallel to the struts.

8. The aortic graft of claim 1 further comprising the upper end of said tubular material having a resilient ring integral therewith which ring is capable of being compressed to a size smaller than its normal diameter.

9. The aortic graft of claim 1 further comprising a bifurcated structure wherein the flexible tubular material has two legs, one of said legs being shorter than the other.

* * * * *

UNITED STATES PATENT AND TRADEMARK OFFICE
CERTIFICATE OF CORRECTION

PATENT NO. : 4,562,596

DATED : January 7, 1986

INVENTOR(S) : Elliot Kornberg

It is certified that error appears in the above-identified patent and that said Letters Patent is hereby corrected as shown below:

Sheet 1 of the drawings, consisting of Figs. 2 and 5, should be deleted to be replaced with the sheet of drawings, consisting of Figs. 2 and 5, as shown on the attached page.

Sheet 1, FIG. 2 should appear as follows:

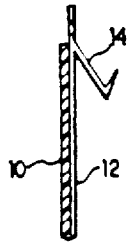

FIG. 2

Sheet 1, FIG. 5 should appear as follows:

FIG. 5

UNITED STATES PATENT AND TRADEMARK OFFICE
CERTIFICATE OF CORRECTION

PATENT NO. : 4,562,596

DATED : January 7, 1986

INVENTOR(S) : Elliot Kornberg

It is certified that error appears in the above-identified patent and that said Letters Patent is hereby corrected as shown below:

Column 3, line 19, after "length" add -- or beyond the length --.

Signed and Sealed this

Sixteenth Day of November, 1993

*Attest:*

BRUCE LEHMAN

*Attesting Officer*     *Commissioner of Patents and Trademarks*